United States Patent

Hibert et al.

[11] Patent Number: 4,612,312
[45] Date of Patent: Sep. 16, 1986

[54] GLUTARIMIDE ANTIANXIETY AND ANTIHYPERTENSIVE AGENTS

[75] Inventors: Marcel Hibert; Maurice W. Gittos, both of Strasbourg, France

[73] Assignee: Merrell Dow Pharmaceuticals Inc., Cincinnati, Ohio

[21] Appl. No.: 743,395

[22] Filed: Jun. 13, 1985

Related U.S. Application Data

[63] Continuation-in-part of Ser. No. 635,394, Jul. 30, 1984, abandoned.

[51] Int. Cl.[4] .................. C07D 405/12; A61K 31/395
[52] U.S. Cl. ..................................... 514/225; 514/234; 514/255; 514/278; 514/321; 514/322; 546/16; 546/197; 546/198; 546/199; 544/6; 544/52; 544/70; 544/105; 544/230; 544/353
[58] Field of Search ............... 546/197, 198, 199, 16; 514/225, 255, 234, 278, 321, 322; 544/6, 52, 70, 105, 230, 353

[56] References Cited

U.S. PATENT DOCUMENTS

| | | | |
|---|---|---|---|
| 2,725,386 | 11/1955 | Bovet et al. | 546/197 |
| 3,717,634 | 2/1973 | Wu et al. | 546/16 |
| 4,182,763 | 1/1980 | Casten et al. | 546/16 |

Primary Examiner—Robert T. Bond
Attorney, Agent, or Firm—Stephen L. Nesbitt; William J. Stein

[57] ABSTRACT

Glutarimide derivatives of the formula which are useful antihypertensive and antianxiety agents

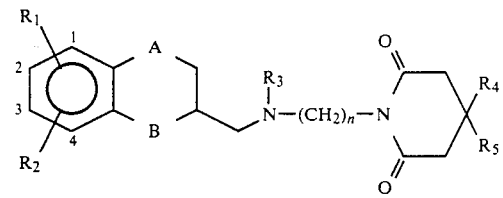

wherein $R_1$ and $R_2$ each independently represent hydrogen, a 1 to 4 carbon alkyl, a 1 to 4 carbon alkoxy, halogen, nitro, hydroxy, $SO_3H$, $SO_2NH_2$, and when $R_1$ and $R_2$ are taken together, form a fused phenyl group at the 1,2- or 3,4- positions, with the proviso that when $R_1$ and $R_2$ are identical they each represent a hydrogen, a 1 to 4 carbon alkyl, a 1 to 4 carbon alkoxy, hydroxy or a halogen group; A and B independently represent an oxo, a thio or an imino group having the formula $-N(R_6)-$ wherein the $R_6$ group is hydrogen or a 1 to 4 carbon alkyl group; $R_3$ is a hydrogen, a 1 to 4 carbon alkyl or hydroxyethyl group; n is an integer of from 2 to 5; and $R_4$ and $R_5$ represent methyl groups or when taken together form a cyclopentane or cyclohexane ring; its enantiomers; and the pharmaceutically acceptable acid addition salts thereof.

12 Claims, No Drawings

GLUTARIMIDE ANTIANXIETY AND ANTIHYPERTENSIVE AGENTS

This application is a continuation-in-part application of Ser. No. 635,394, filed July 30, 1984, now abandoned.

FIELD OF THE INVENTION

This invention relates to certain glutarimide derivatives and their use as antianxiety and antihypertensive agents.

BACKGROUND

Anxiety has been defined as an apprehension or concern regarding some future event. Most, if not all, people occasionally suffer some symptoms of anxiety in response to appropriate stimuli. In some individuals, these feelings of anxiety or panic in response to the everyday pressures of life can be overwhelming, rendering the individual an unproductive member of society. Whereas individual group counseling represents the preferred primary mode of therapy, the use of chemotherapeutic agents has proven to be a useful adjunct in the treatment of anxiety, enabling a seriously afflicted individual to regain productive status while undergoing concurrent psychotherapy.

Compounds of the class of benzodizepines are currently the therapeutic agents of choice in the treatment of anxiety. In particular, chlordiazepoxide, diazepam and oxazepam are commonly used. However, this class of compounds has a great potential for misuse, particularly among the class of patients undergoing therapy. Moreover, the benzodiazopines generally possess undesired sedative effects and detracting interactions with other drugs, including for example, alcohol.

Buspirone, a recently developed non-benzodiazepine antianxiety agent, is reported to be largely free of these undesirable characteristics. However, it also suffers certain drawbacks. More particularly, Buspirone is thought to affect dopamine receptors with the resultant manifold display of side effects. Applicants have discovered a class of novel glutarimide antianxiety agents that are generally free from the side effects of Buspirone and the benzodiazepines.

SUMMARY OF THE INVENTION

Accordingly, this invention is directed to glutarimide derivatives of general Formula I

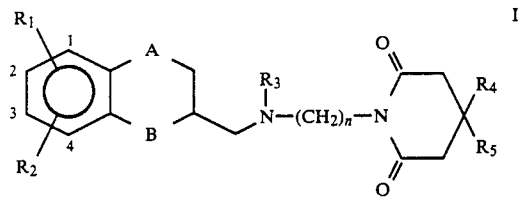

wherein $R_1$ and $R_2$ each independently represent hydrogen, a 1 to 4 carbon alkyl, a 1 to 4 carbon alkoxy, halogen, nitro, hydroxy, $SO_3H$, $SO_2NH_2$, and when $R_1$ and $R_2$ are taken together, form a fused phenyl group at the 1,2- or 3,4-positions, with the proviso that when $R_1$ and $R_2$ are identical they each represent a hydrogen, a 1 to 4 carbon alkyl, a 1 to 4 carbon alkoxy, hydroxy or a halogen group; A and B independently represent an oxo, a thio or an imino group having the formula $—N(R_6)—$ wherein the $R_6$ group is hydrogen or a 1 to 4 carbon alkyl group; $R_3$ is a hydrogen, a 1 to 4 carbon alkyl or hydroxyethyl group; n is an integer of from 2 to 5; and $R_4$ and $R_5$ represent methyl groups or when taken together form a cyclopentane or cyclohexane ring; its enantiomers; and the pharmaceutically acceptable acid addition salts thereof.

DESCRIPTION OF THE PREFERRED EMBODIMENTS

As used herein the term "a 1 to 4 carbon alkyl group" is taken to mean a straight or branched alkyl group of from 1 to 4 carbon atoms. Illustrative examples of a 1 to 4 carbon alkyl group as used herein are methyl, ethyl, n-propyl, isopropyl, n-butyl and isobutyl.

Similarly, the term "a 1 to 4 carbon alkoxy group" is taken to mean a straight or branched alkoxy group of from 1 to 4 carbon atoms. Illustrative examples of a 1 to 4 carbon alkoxy group as used herein are methoxy, ethoxy, n-propoxy, isopropoxy, n-butoxy, and isobutoxy.

The term "halogen group" is taken to mean a fluorine, chlorine or bromine atom.

The expression "pharmaceutically acceptable acid addition salts" is intended to apply to any non-toxic organic or inorganic acid addition salt of the base compounds represented by Formula I. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Either the mono or the di-acid salts can be formed, and such salts can exist in either a hydrated or a substantially anhydrous form. In general, the acid addition salts of these compounds are crystalline materials which are soluble in water and various hydrophilic organic solvents, which in comparison to their free base forms, generally demonstrate higher melting points and an increased chemical stability.

Preferred compounds of this invention are those compounds of Formula I wherein A and B are oxo. Other preferred compounds are those compounds of Formula I wherein $R_3$ is hydrogen, or compounds wherein n represents the integer 4, or compounds wherein $R_4$ and $R_5$ represent methyl groups or when taken together form a cyclopentane ring.

Another preferred group of compounds are those compounds of Formula I wherein A and B are independently an oxo or an imino group having the Formula $—N(R_6)—$, wherein $R_6$ is hydrogen or a 1 to 4 carbon alkyl group.

Yet another preferred group of compounds are those wherein $R_1$ and $R_2$ are taken together to form a fused phenyl ring fused to the 1,2- or 3,4-positions designated at the terminal phenyl ring of Formula I; A and B are oxo and $R_3$ represents hydrogen.

The most preferred compounds of this invention are those compounds of Formula I wherein $R_1$, $R_2$ and $R_3$ are hydrogen atoms, A and B are both oxo groups, n is either the integer 2 or 4, and $R_4$ and $R_5$ taken together form a cyclopentane ring, that is the compounds 8-[2-

(1,4-benzodioxan-2-ylmethylamino)ethyl]-8-azas-piro[4,5]decane-7,9-dione and 8-[4-(1,4-benzodioxan-2-ylmethylamino)butyl]-8-azaspiro[4,5]decane-7,9-dione, respectively.

The Formula I glutarimide derivatives of this invention are prepared in any manner by standard techniques analogously known by those skilled in the art. The compounds of this invention are prepared by condensation of an appropriate heterocyclomethylamino nucleophile of Formula II with a glutarimide substrate of Formula III as outlined in Scheme I

SCHEME I

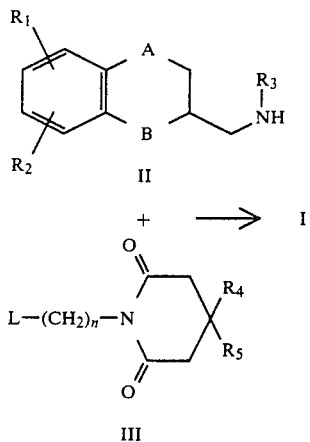

wherein $R_1$, $R_2$, $R_3$, $R_4$, $R_5$, A, B and n are as defined above in Formula I and L represents a suitable leaving group. This simple nucleophilic condensation reaction is preferably performed by allowing approximately equimolar amounts of the nucleophile (II) and the substrate (III) to react from about 1 hour to about 24 hours, depending upon the reactants, the solvent and the temperature at which the reaction is conducted. The reaction temperature can range from 25° C. to about 150° C., preferably from about 60° C. to about 150° C.

Inasmuch as the reactants employed are typically crystalline solids, the use of solvents in this reaction is preferred. Suitable solvents include any non-reactive solvent, preferably those having a boiling point in the range of from 60° C. to 150° C., as for example, petroleum ethers; chlorinated hydrocarbons such as carbon tetrachloride, ethylene chloride, methylene chloride or chloroform; chlorinated aromatics such as 1,2,4-trichlorobenzene, or o-dichlorobenzene; carbon disulfide; and ethereal solvent such as diethylether, tetrahydrofuran or p-dioxane; and aromatic solvent such as benzene, toluene or xylene; or an alcoholic solvent such as ethanol. Especially preferred solvents are those known to promote nucleophilic reactions such as dimethysulfoxide and dimethylformamide.

The product of Formula I can then be isolated by any appropriate techniques, such as filtering to remove any solid materials and subsequently evaporating the solvent from the filtrate. The glutarimides of Formula I can be purified, for example, using their picric or oxalic acid complexes by standard techniques known to the art.

The nucleophilic primary amine of Structure II wherein $R_3$ is hydrogen can readily be prepared, for example, by the reduction of the corresponding cyano derivative of Structure IV

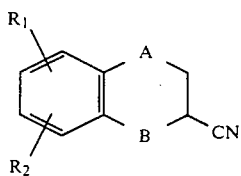

wherein $R_1$, $R_2$, A and B are as defined above for Structure I. This reduction can be acomplished with a number of reagent systems including catalytic reductions employing hydrogen gas and a catalytic metal such as palladium on charcoal, Raney nickel, platinum, rhodium, ruthenium or platinum oxide; diborane; sodium borohydride; dissolving metal reductions utilizing lithium, sodium, potassium, calcium, zinc, magnesium, tin or iron in liquid ammonia or a low-molecular weight aliphatic amine or sodium, aluminum or zinc amalgam, zinc, tin or iron in a hydroxylic solvent or in the presence of an aqueous mineral acid; or lithium aluminum hydride.

The Structure II nucleophiles can be prepared by allowing the Structure IV cyano compounds to react with 1 to 2 molar equivalents, preferably about 1.5 molar equivalents, of lithium aluminum hydride in a suitable sovlent. The reaction is allowed to proceed from about 30 minutes to about 24 hours, preferably from about 1 to 5 hours, depending upon the reactants, the solvent and temperature. Suitable temperatures are from −78° C. to 60° C., preferably about 20° C. Suitable solvents include ethereal solvents such as diethyl ether, tetrahydrofuran (THF), p-dioxane, 1,2-dimethoxyethane (DME), diglyme or an aromatic solvent such as benzene, toluene or xylene.

Secondary amines of Formula II, wherein $R_3$ is other than hydrogen can be prepared by one of two methods:

(a) direct alkylation of the corresponding primary amine (Formula II, $R_3$=H) with a suitable alkyl halide, tosylate or mesylate in an appropriate solvent, such as acetonitrile, and in the presence of one equivalent or an excess of an organic or inorganic base such as potassium carbonate; or (b) the acylation of the corresponding primary amine (Formula II, $R_3$=H) with an appropriate acid chloride in an appropriate solvent such as methylene chloride in the presence of one or more molar equivalents of an organic nitrogen base such as a tri(lower alkyl) amine, for example triethylamine, or an aromatic amine, such as pyridine. Pyridine can be employed in large excess, and thereby serve also in the capacity of the reaction solvent. The amine so obtained can be reduced to the corresponding secondary amine of Formula II utilizing standard procedures such as via reduction with diborane or lithium aluminum hydride.

Many of the cyano derivatives of Structure IV are known in the prior art. Applicants have prepared these cyano derivatives by reacting a compound of Structure V

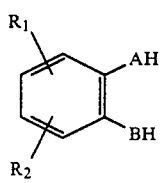

wherein $R_1$, $R_2$, A and B are as defined in Structure I, with 2-bromo or preferably 2-chloroacrylonitrile. Approximately equimolar amounts of the Structuve V compound and the acrylonitrile, are mixed with 2 or more molar equivalents of a base such as potassium carbonate in a suitable solvent. The reaction is allowed to proceed at a temperature of from 0° C. to the boiling point of the reaction mixture for a period of from 1 to 24 hours. Suitable solvents include dimethylformamide; dimethylsulfoxide; acetone; chlorinated hydrocarbons such as carbon tetrachloride, chloroform or methylene chloride; ethereal solvents such as diethylether, tetrahydrofuran (THF) or diglyme; aromatic solvents such as benzene, toluene or xylene; or alcoholic solvents such as methanol or ethanol.

Where A and B represent different atoms, or where $R_1$ and $R_2$ are different, a mixture of products will be obtained. These mixtures can be readily separated and purified by methods commonly known to those skilled in the art, such as by chromatography on silica gel or fractional recrystalization. Furthermore, when the $R_1$ or $R_2$ groups of a Structure V compound are a hydroxy group, this hydroxy group must be protected prior to undergoing the above described condensation reaction with 2-bromo- or 2-chloroacrylonitrile. Suitable protecting groups include benzyl or methyl groups and removal is preferably accomplished on the corresponding compound of Structure II. The removal of the protecting group can be by any suitable means generally known to the art, such as by catalytic reduction of the benzyl group or by treatment with an acid such as hydrobromic acid or boron tribromide.

The leaving groups of the Structure III compounds can be any group known to those skilled in the art, as for example an ester of a sulfuric or sulfonic acid such as a tosylate (OTS) or mesylate (OMS); an iodide, bromide or chloride; or a hydroxyl group. Applicants have prepared the Structure III substrates wherein L is a tosylate by treating the corresponding alcohol of structure VI.

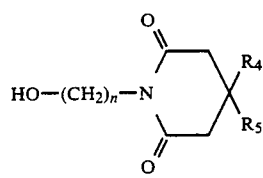

VI wherein $R_4$, $R_5$ and n are as defined for Structure I, with a base such as potassium carbonate and subsequently adding a slight molar excess of tosyl chloride. The reaction temperature ranges from $-78°$ C. to about 60° C. and preferably from 0° C. to room temperature. The reaction is allowed to proceed for about 1 hour to about 12 hours depending on the reactants, the temperature and the solvent. Suitable solvents include dimethylformamide; dimethylsulfoxide; acetone, aromatic solvents such as benzene, toluene or xylene; or an ethereal solvent such as diethyl ether, tetrahydrofuran (THF) or 1,2-dimethoxyethane (DME). A hydrogen halide acceptor is preferably employed to react with the hydrogen halide that forms during the reaction. For this purpose, one or more molar equivalents of an organic nitrogen base can be employed. Suitable organic nitrogen bases include tri(lower alkyl)amines such as triethylamine, or an aromatic amine such as pyridine, a picoline or a collidine. Pyridine and the picolines and collidines can be utilized in a large excess, serving also as the reaction solvent.

Applicants have prepared the Structure VI alcohols by reacting approximately equimolar amounts of an hydroxyalkylamine of Structure VII

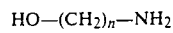

wherein n is as defined in Structure I, with a glutaric anhydride of Structure VIII

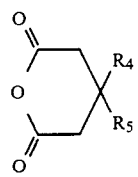

VIII wherein $R_4$ and $R_5$ are as defined in Structure I. Preferably a slight excess of either the hydroxyamine or the glutaric anhydride is employed. If one conducts this reaction in a solvent such as benzene or toluene, the water formed during the course of the reaction can be continuously removed, for example, by means of a Dean-Stark apparatus, thereby driving the amidation reaction to completion. The reaction is allowed to proceed at the reflux temperature of the reaction mixture for a period of from 12 to 24 hours. The crude product can be subsequently isolated by simple removal of solvent.

The structure I compounds are useful therapeutic agents possessing antianxiety and antihypertensive properties. The compounds of this invention can be administered either orally, parenterally such as subcutaneously, intravenously, intramuscularly or intraperitoneally or rectally. The preferred route of administration of the compounds of this invention is orally. The quantity of novel compound administered will vary depending on the patient, the mode of administration and severity of the anxiety or hypertension to be treated and can be any effective amount. Repetitive daily administration of the compounds may be desired and will vary with the patient's condition and the mode of administration.

For oral administration, the antianxiety effective amount of a Structure I compound is from 0.005 to 10 mg/kg of patient body weight per day, preferably from 0.05 to 5 mg/kg of patient body weight per day. The preferred antianxiety dose of the Structure I compound wherein $R_1$, $R_2$ and $R_3$ are hydrogen atoms, A and B are oxygen atoms, n is 4 and $R_4$ and $R_5$ together form a cyclopentane ring is about 0.1 mg/kg of patient body weight per day. Pharmaceutical compositions in unit dose form can contain from 1 to 50 mg of active ingredient and can be taken one or more times per day.

For parenteral administration, an antianxiety effective amount of a Structure I compound is from about 0.005 to 10 mg/kg of patient body weight per day, preferably from about 0.05 to 5 mg/kg of patient body weight per day. A parenteral composition in unit dose form can contain from 0.1 mg to 10 mg of active ingredient and can be taken one or more times per day.

An antihypertensive effective amount of the active ingredient can range from about 0.005 to 10 mg/kg of patient body weight per day, preferably from 0.05 to 5 mg/kg of patient body weight per day. An antihypertensive composition in unit does form can contain from about 1 to 50 mg of active ingredient, preferably from about 5 to 25 mg of active ingredient, and can be taken one or more times per day.

As used herein with respect to the treatment of anxiety symptoms, the term patient is taken to mean a human. As used herein with respect to the treatment of hypertension the term patient is taken to mean warm blooded animals, for example birds, such as chickens and turkeys, in addition to mammals, such as primates, humans, sheep, horses, bovines, pigs, dogs, cats, rats and mice.

For oral administration the compounds can be formulated into solid or liquid preparations such as capsules, pills, tablets, lozenges, melts, powders, solutions, suspensions or emulsions. The solid unit dosage forms are those generally employed such as capsules or tablets. Capsules can be of the ordinary gelatin type containing additional excipients such as, surfactants, lubricants and inert fillers such as lactose, sucrose, and cornstarch. In another embodiment the compounds of Structure I can be tableted with conventional tablet bases such as lactose, sucrose, and cornstarch in combination with binders, such as acacia, cornstarch or gelatin, disintegrating agents such as potato starch or alginic acid, and lubricants such as stearic acid or magnesium stearate.

For parenteral administration the compounds may be administered as injectable dosages of a solution or suspension of the compound in a physiologically acceptable diluent with a pharmaceutical carrier. Suitable diluents or carriers include sterile liquids such as water or oils, with or without the addition of surfactants or other pharmaceutically acceptable adjuvants. Illustrative of various oils which can be employed in the practise of this invention are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solution.

The following specific examples further illustrate the preparation of compounds employed in the instant invention.

EXAMPLE I

2-Cyanobenzodioxan[1,4]

Pyrocatechol (12 g, 0.11 mole), potassium carbonate (41.1 g, 0.3 mole) and 2-chloroacrylonitrile (8 ml, 0.1 mole) are mixed in acetone (200 ml) and boiled at the reflux for 18 hours under a nitrogen atmosphere. the mixture is cooled, the solid filtered off and the solvent evaporated under reduced pressure. The oily residue is dissolved in methylene chloride, washed with water, potassium hydroxide (5%) and hydrochloric acid (5%). The organic solution is dried over sodium sulphate and concentrated. The residual oil (15.73 g) is then distilled (120° C., 0.05 mm Hg) to give a colorless oil (13.25 g) which then crystallizes to the title compound (yield: 83%).

m.p.: 54° C.

NMR (CDCl$_3$, 60 MH$_z$): 6.85 ppm (b.s., 4 H, aromatic); 5.05 ppm (t, 1 H, CH); 4.25 ppm (d, 2 H, CH$_2$).

EXAMPLE 2

2-aminomethyl-benzodioxan[1,4]

2-cyano-benzodioxan[1,4] (13.2 g, 82 mM) dissolved in dry tetrahydrofuran (THF) (150 ml) is added dropwise at 0° C., under nitrogen atmosphere, to LiAlH$_4$ (4.91 g, 122 mM) suspended in dry THF (100 ml). The mixture is warmed to reflux for 1.5 hours, then cooled in an ice bath. Hydrolysis is performed by adding dropwise a saturated solution of NH$_4$Cl. Dry sodium sulfate is added and solids are filtered off to afford after evaporation of the solvent a yellow oil (10.1 g). The hydrochloride is made using HCl gas in dry Et$_2$O. The solid title compound obtained is recrystallized in a MeOH-/AcOEt mixture (Yield: 60%).

m.p.: 220° C.

EXAMPLE 3

2-(N-isopropyl)-aminomethyl-benzodioxan[1,4]

2-aminomethyl-benzodioxan[1,4] (II, R$_3$=H, 1 g, 6 mM), isopropyl iodide (67 ml) and an excess of potassium carbonate are mixed into acetonitrile and refluxed under stirring for 48 hours. The solid residue is filtered off and the filtrate concentrated providing 1.34 g of a crude red oil. Flash chromatography on silica (MeOH/CH$_2$Cl$_2$ 8/92) afforded 0.97 g (78%) of the pure product. The hydrochloride is recrystallized in i-PrOH/AcOEt giving white crystals.

m.p.: 188° C.

EXAMPLE 4

2-(N-n-propyl)-aminomethyl-benzodioxan[1,4]

(a) 2-Aminomethyl-benzodioxan[1,4] (II, R$_3$=H, 0,826 g, 5 mM) are dissolved in 25 ml of methylene chloride under Argon atmosphere and stirred at 0° C. Propionyl chloride (0.5 ml, 5.5 mM) and triethylamine (0.77 ml, 5.5 mM) in 5 ml of methylene chloride is added dropwise. The mixture is stirred 30 min. at room temperature. The organic solution is then washed with aqueous potassium carbonate and diluted hydrochloric acid solutions, dried over sodium sulphate and evaporated, leading after flash chromatography (silica, eluent AcOEt/CH$_2$Cl$_2$=1/1.5 to the desired product (1.05 g, 95%).

(b) The above amide (1.05 g, 4,75 mM) is dissolved in 25 ml of dry tetrahydrofuran (THF) and then added slowly to LiAlH$_4$ (0.284 g, 7.12 mM) in 5 ml of dry THF under an argon atmosphere. The mixture is stirred during 4.5 hours under reflux. The hydride in excess is hydrolysed by a saturated solution of ammonium chloride. The mixture is then filtered on dry sodium sulphate and the filtrate concentrated to give 1.25 g of a colorless oil. This oil is purified by extractions to afford 0.85 g (86%) of 2-(N-n-propyl)-aminomethyl-benzodioxan[1,4]. The hydrochloride is recrystallized in i-propanol.

m.p.: 184° C.

EXAMPLE 5

N-(4-Hydroxybutyl)-3,3-tetramethylene glutarimide

4-Hydroxybutylamine (30 ml, 318.9 mM) is added to a solution of 3,3-tetramethylene glutaric anhydride (56.35 g, 335 mM) in dry toluene (650 ml). The mixture is heated to reflux with a Dean-Stark apparatus during 20 hours. The mixture is cooled, the solvent evaporated and the residue dissolved in ethyl acetate. This organic phase is washed with HCl 5%, NaOH 5%, brine and dried over sodium sulfate. The solvent is evaporated under reduced pressure affording the title compound as a sticky yellow oil (68.1 g). Flash chromatography with a 5:3 mixture of ethyl acetate and methylene chloride as eluent allowed the preparation of pure V (56% yield) as a colorless oil (43 g).

EXAMPLE 6

N-(4-tosyloxybutyl)-3,3-tetramethylene glutarimide

N-(4-hydroxybutyl)-3,3-tetramethylene glutarimide (43 g, 179.6 mM) is dissolved in pyridine (600 ml). Potassium carbonate (50 g) is added. The mixture is cooled to 0° C. in an ice bath and tosyl chloride (36.5 g, 197.5 ml) is slowly added under an inert atmosphere. The reaction mixture is stirred during 1 hour at 0° C. and 4.5 hours at room temperature. The end of the reaction is checked by thin layer chromatography. Inorganic salts are filtered off, pyridine is evaporated under vacuum and the oily residue is dissolved in methylene chloride, washed with water, aqueous sodium carbonate and water again. Drying over sodium sulfate and evaporation of the solvent affords a crude red oil (55.2 g, 81%). Flash chromatography on silica ($CH_2Cl_2$/AcOEt 5/1) yields pure title compound (39.7 g, 58%) as a yellow oil which crystallizes on standing.

m.p.: 58° C.

EXAMPLE 7

8-[4-(1,4-benzodioxan-2-ylmethylamino)butyl]-8-azaspiro[4,5] decane-7,9-dione

2-Aminomethyl-benzodioxane[1,4] (0.97 g, 4.8 mM) is dissolved in dry dimethylformamide (DMF) (5 ml). Potassium carbonate (2 g) is added. N-(4-Tosyloxybutyl)-3,3-tetramethylene glutarimide (1.84 g, 4.8 mM) dissolved in dry dimethylformamide (DMF) (25 ml) is slowly added under stirring and inert atmosphere. The mixture is stirred overnight at 120° C. The solid is filtered off and DMF is distilled under reduced pressure. The oily residue is dissolved in ethyl acetate, washed with $H_2O$, extracted with HCl, 5%, basified with potassium carbonate and extracted with ethyl acetate. This organic solution is finally washed with brine, dried over sodium sulfate and the solvent is removed under vacuum yielding a yellow oil. This crude material is purified by flash chromatography on silica gel (AcOEt/MeOH 5/1 to 1/1) leading to pure title compound (160 mg). Additional pure material is obtained from the first extracts. The salt is formed in HCl/$Et_2O$ and recrystallized in isopropanol/ethyl acetate/ether yielding slightly yellow needles.

m.p.: 191° C.

Following essentially the same procedure but substituting N-methyl-2-aminomethyl-benzodioxane[1,4]; N-ethyl-2-aminomethyl-benzodioxane[1,4]; N-n-propyl-2-aminomethyl-benzodioxane[1,4]; or N-i-propyl-2-aminomethyl-benzodioxane[1,4] for the 2-aminomethyl-benzodioxane [1,4] above, the following compounds are respectively obtained:

8-[4-(1,4-benzodioxan-2-ylmethyl-N-methylamino)-butyl]-8-azaspiro[4,5]decane-7,9-dione, hydrochloride salt, 0.75 $H_2O$, m.p.: 50° C.;

8-[4-(1,4-benzodioxan-2-ylmethyl-n-ethylamino)butyl]-8-azaspiro[4,5]decane-7,9-dione, oxalate, 0.5$H_2O$, m.p.: 136° C.;

8-[4-(1,4-benzodioxan-2-ylmethyl-N-n-propylamino)-butyl]-8-azaspiro[4,5]decane-7,9-dione, oxalate, m.p.: 121° C.;

8-[4-(1,4-benzodioxan-2-ylmethyl-N-isopropylamino)-butyl]-8-azaspiro[4,5]decane-7,9-dione, oxalate, m.p.: 133° C.;

Following essentially the same procedure, but substituting the compound 2-aminomethyl-benzoxazine[1,4] for the 2-aminomethyl-benzodioxane [1,4] above, the compound 8-[4-(1,4-benzoxazine-2-ylmethylamino)-butyl]-8-azaspiro[4,5]decane-7,9-dione was obtained having a melting point of 151° C.

Following essentially the same procedure, but substituting N-(4-tosyloxybutyl)-3,3-dimethylglutarimide for the N-(4-tosyloxybutyl)-3,3-tetramethyleneglutarimide above, results in the preparation of the compound N-[4-(1,4-benzodioxan-2-ylmethylamino)butyl]-3,3-dimethylglutarimide, hydrochloride salt, having a melting point of 153° C.

EXAMPLE 8

(−)8-[4-(1,4-benzodioxan-2-ylmethylamino)butyl]-8-azaspiro[4,5]decane-7,9-dione

8-[4-(1,4-benzodioxan-2-ylmethylamino)butyl]-8-azaspiro[4,5]decane-7,9-dione (0,91 g) is dissolved in a mixture of acetone and isopropanol. (+) Binaphthyl phosphoric acid (BNP) (0.82 g) dissolved in acetone is added to the previous solution, leading to the formation of white crystals, which are are removed by filtration, washed with i-PrOH, EtOH and acetone.

The resulting residue is suspended in water and basified with potassium carbonate. The free base so obtained is extracted with ethyl acetate. The organic extract is dried and evaporated affording the crude optically enriched free base. The remaining traces of BNP, K+ salt are removed by rapid filtration over silica (AcOEt/MeOH=97/3) yielding the pure free base (0.44 g).

The hydrochloride salt is formed in $Et_2O$ and recrystallized in EtOH providing white crystals of the expected product.

m.p.: 200° C. $[\alpha]_D^{20} = -44.8°$ C. ($H_2O$, c=0.460).

By following essentially the same procedure but substituting (−) Binaphthyl phosphoric acid (BNP), for (+) BNP, the remaining enantiomer was obtained: (+)8-|4-(1,4-benzodioxan-2-ylmethylamino)butyl|-8-azaspiro|4,5|decane-7,9-dione, HCl salt.

m.p.: 199° C., $[\alpha]_D^{20} = +45.1°$ C. ($H_2O$, c=0.480).

EXAMPLE 9

8-[2-(1,4-benzodioxan-2-ylmethylamino)ethyl]-8-azaspiro[4,5]decane-7,9-dione

The compound 2-aminomethyl-benzodioxane [1,4] (1 equivalent is dissolved in dry dimethylformamide (DMF). An excess of potassium carbonate is added thereto. N-(2-tosyloxyethyl)-3,3-tetramethylene glutarimide (1 equivalent), dissolved in dry dimethylformamide (25 ml), is slowly added with stirring under an inert atmosphere. The mixture is stirred overnight at 120° C.; the solid is filtered; and the dimethylformamide is removed by distillation under reduced pressure. The oily residue is dissolved in ethyl acetate, washed with $H_2O$ and extracted with HCl 5%. The acid extract is made alkaline with potassium carbonate and extracted with ethyl acetate. The resulting organic extract is washed with brine, dried over sodium sulfate and the solvent is removed under vacuum to yield a yellow oil. This crude material is purified by flash chromatography on silica gel (AcOEt), leading to the pure title compound. The hydrochloride salt is formed in isopropanol with 1 equivalent of concentrated hydrochloric acid. Recrystallization in isopropanol provides white crystals.

m.p.: 177° C.

By following essentially the same procedure but substituting N-(3-tosyloxy n-propyl)- and N-(5-tosyloxy n-pentyl)-3,3-tetramethylene glutarimide for the N-(2-tosyloxyethyl)-3,3-tetramethylene glutarimide above, one obtains the compounds 8-[3-(1,4-benzodioxan-2-ylmethylamino)n-propyl]-8-azaspiro|4,5|decane-7,9-dione.

m.p.:176° C.; and 8-[5-(1,4-benzodioxan-2-ylmethylamino)n-pentyl]-8-azaspiro[4,5]decane-7,9-dione.

m.p.:156° C.; respectively.

EXAMPLE 10

2,3-dihydro-naphtho[1,2b]dioxin-2 and 3-ylnitrile

The compound 1,2-Dihydroxynaphthalene (2 g, 11.2 mM), 2-chloro acrylonitrile (0.95 ml) and potassium carbonate (4.9 g, 35.4 mM) are mixed in 40 ml of dry acetone under argon, and refluxed for 18 hours. The solid residue is filtered, and the filtrate evaporated to dryness. The reddish oil residue is dissolved in ethyl acetate and this solution is washed successively with water, dilute potassium hydroxide, hydrochloric acid solutions and brine, dried over sodium sulphate and evaporated to dryness. The remaining oil so obtained (2.17 g) is purified by flash chromatography (silica, toluene/hexane 2/1) to yield 1.58 g (67%) of a white solid, which is a mixture of the two possible isomers.

EXAMPLE 11

2- and 3-(aminomethyl)-2,3-dihydronaphtho[1,2,b]dioxin

The mixture of 2,3-dihydronaphtho[1,2,b]dioxin-2 and 3-ylnitrile, as obtained in the preceeding example, is dissolved in 30 ml of dry THF. This solution is slowly added to a suspension of LiALH$_4$ (0.45 g, 11.2 mM) contained in 5 ml of dry THF, at 0° C., under an atmosphere of argon. The mixture is stirred for 3 hours at room temperature, hydrolysed with a saturated solution of ammonium chloride, diluted with methylene chloride, filtered and dried over anhydrous sodium sulfate.

The oil which is obtained following evaporation (1.61 g) is repetitively flash chromatographed on silica (CH$_2$Cl$_2$, MeOH 9/1) to produce the two almost pure separated isomers.

EXAMPLE 12

8-[4-(2,3-dihydro-naphtho[1,2,b]dioxin-2-ylmethylamino)butyl-8-azaspiro[4,5]decane-7,9-dione The less polar isomer of the 2,3-dihydro-2-methylamino or 3-aminomethylnaphtho (1,2,b)dioxins (0.676 g, 3.1 mM), iodide of Formula III (n=4; R$_4$, R$_5$=cyclopentyl) (1.096 g, 3.1 mM) and an excess of potassium carbonate are mixed in 30 ml of dry dimethylformamide (DMF) under an argon atmosphere. After warming 17 hours at 100° C., the mixture is filtered, DMF is evaporated, the residual oil dissolved in AcOEt, washed with water and extracted with diluted hydrochloric acid. The resulting solution is made alkaline and extracted with AcOEt. The organic phase is dried on sodium sulfate and evaporated to provide 1.53 g of a crude oil.

Purification by flash chromatography on silica (MeOH/CH$_2$Cl$_2$ 5/95) affords 0.62 g of the pure product. The hydrochloride is recrystallized in AcOH/CH$_2$Cl$_2$/i-PrOH.

m.p.: 228° C.

Following essentially the same procedure but substituting the most polar isomer of the 2,3-dihydro-aminomethylnaphtho[1,2,b]dioxino for the less polar isomer of the same mixture, one obtains the other pure isomer.

m.p.: 222° C.

We claim:

1. A glutarimide having the formula

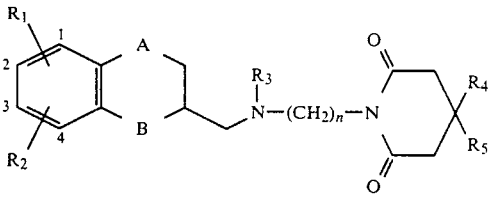

wherein R$_1$ and R$_2$ each independently represent hydrogen, a 1 to 4 carbon alkyl, a 1 to 4 carbon alkoxy, halogen, nitro, hydroxy, SO$_3$H, SO$_2$NH$_2$, and when R$_1$ and R$_2$ are taken together, form a fused phenyl group at the 1,2- or 3,4- positions, with the proviso that when R$_1$ and R$_2$ are identical they each represent a hydrogen, a 1 to 4 carbon alkyl, a 1 to 4 carbon alkoxy, hydroxy or a halogen group; A and B independently represent an oxo, a thio or an imino group having the formula —N(R$_6$)— wherein the R$_6$ group is hydrogen or a 1 to 4 carbon alkyl group; R$_3$ is a hydrogen, a 1 to 4 carbon alkyl or hydroxyethyl group; n is an integer of from 2 to 5; and R$_4$ and R$_5$ represent methyl groups or when taken together form a cyclopentane or cyclohexane ring; its enantiomers; and the pharmaceutically acceptable acid addition salts thereof.

2. A glutarimide according to claim 1 wherein A and B are oxo.

3. A glutarimide according to claim 1 wherein R$_3$ is hydrogen.

4. A glutarimide according to claim 1 wherein n is the integer 4.

5. A glutarimide according to claim 1 wherein R$_4$ and R$_5$ represent methyl groups or when taken together form a cyclopentane ring.

6. A glutarimide according to claim 1 wherein A and B are independently an oxo or an imino group having the formula —N(R$_6$)— wherein R$_6$ is hydrogen or a 1 to 4 carbon alkyl group.

7. A glutarimide according to claim 1 wherein R$_6$ is hydrogen.

8. A glutarimide according to claim 1 wherein R$_1$ and R$_2$ taken together form a fused phenyl group at the 1,2- or 3,4- position; A and B are oxo and R$_3$ is hydrogen.

9. A glutarimide according to claim 1 that is the compound 8-[4-(1,4-benzodioxan-2-ylmethylamino)butyl]-8-azaspiro[4,5]decane-7,9-dione, its enantiomers, and the pharmaceutically acceptable acid addition salts thereof.

10. A glutarimide according to claim 1 that is the compound 8-[2-(1,4-benzodioxan-2-ylmethylamino)ethyl]-8-azaspiro[4,5]decane-7,9-dione, its enantiomers, and the pharmaceutically acceptable acid addition salts thereof.

11. A method for relieving the symptoms of anxiety in a patient in need thereof, which comprises administering to said patient an anxiolytic effective amount of a compound of claim 1.

12. An anxiolytic or antihypertensive composition comprising an anxiolytic or antihypertensive effective amount of a glutarimide compound according to claim 1, its enantiomer or a pharmaceutically acceptable acid addition salt thereof, in combination with a pharmaceutically acceptable carrier or diluent.

* * * * *